(12) United States Patent
Friedman et al.

(10) Patent No.: US 6,626,926 B2
(45) Date of Patent: Sep. 30, 2003

(54) METHOD FOR DRIVING AN ULTRASONIC SYSTEM TO IMPROVE ACQUISITION OF BLADE RESONANCE FREQUENCY AT STARTUP

(75) Inventors: Allan L. Friedman, Cincinnati, OH (US); William T. Donofrio, Cincinnati, OH (US); Eitan T. Wiener, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 43 days.

(21) Appl. No.: 09/866,948

(22) Filed: May 29, 2001

(65) Prior Publication Data

US 2002/0049462 A1 Apr. 25, 2002

Related U.S. Application Data

(60) Provisional application No. 60/241,895, filed on Oct. 20, 2000.

(51) Int. Cl.[7] ............................................... A61B 17/32
(52) U.S. Cl. ........................................ 606/169; 604/22
(58) Field of Search ................................ 606/169, 170, 606/171; 604/22, 28

(56) References Cited

U.S. PATENT DOCUMENTS

| | | | | |
|---|---|---|---|---|
| 2,917,691 A | | 12/1959 | DePrisco et al. ............ 318/118 |
| 5,001,649 A | | 3/1991 | Lo et al. ..................... 364/484 |
| 5,026,387 A | * | 6/1991 | Thomas .................. 310/316.01 |
| 5,112,300 A | * | 5/1992 | Ureche ................... 310/323.18 |
| 5,151,085 A | * | 9/1992 | Sakurai et al. .......... 310/316.02 |
| 5,180,363 A | | 1/1993 | Idemoto et al. ................ 202/32 |
| 5,400,267 A | | 3/1995 | Denen et al. ................. 364/552 |
| 5,425,704 A | | 6/1995 | Sakurai et al. ................. 604/22 |
| 5,449,370 A | | 9/1995 | Vaitekunas ................... 606/169 |
| 5,630,420 A | | 5/1997 | Vaitekunas ............... 128/662.03 |
| 5,637,947 A | * | 6/1997 | Kising et al. ........... 310/316.01 |
| 5,707,369 A | | 1/1998 | Vaitekunas et al. ............ 606/31 |
| 5,879,364 A | | 3/1999 | Bromfield et al. ........... 606/169 |
| 5,897,569 A | * | 4/1999 | Kellogg et al. ......... 310/316.01 |
| 5,938,633 A | * | 8/1999 | Beaupre ........................ 604/22 |
| 5,968,007 A | | 10/1999 | Simon et al. .................. 604/22 |
| 6,017,354 A | | 1/2000 | Culp et al. ................... 606/170 |
| 6,019,775 A | * | 2/2000 | Sakurai ....................... 433/119 |
| 6,066,135 A | * | 5/2000 | Honda ............................ 601/2 |
| 6,090,123 A | | 7/2000 | Culp et al. ................... 606/180 |

FOREIGN PATENT DOCUMENTS

JP        2000-175926         6/2000

* cited by examiner

Primary Examiner—Kevin T. Truong
Assistant Examiner—Victor Nguyen
(74) Attorney, Agent, or Firm—Darby & Darby

(57) ABSTRACT

The ability of an ultrasonic system to sweep and lock onto a resonance frequency of a blade subjected to a heavy load at startup is improved by applying a high drive voltage or a high drive current while systematically increasing the level of the applied signal. Increasing the drive signal to the hand piece results in an improved and more pronounced "impedance spectrum." That is, under load, the increased drive signal causes the maximum phase margin to become higher and the minimum/maximum impedance magnitude to become more pronounced. Increasing the excitation drive signal to the hand piece/blade at startup significantly alleviates the limiting factors associated with ultrasonic generators, which results in an increase of the maximum load capability at startup.

9 Claims, 8 Drawing Sheets

METHOD FOR DRIVING AN ULTRASONIC SYSTEM TO IMPROVE ACQUISITION OF BLADE RESONANCE FREQUENCY AT STARTUP

RELATED APPLICATIONS

The present invention relates to, and claims priority of, U.S. Provisional Patent Application Serial No. 60/241,895 filed on Oct. 20, 2000, having the same title as the present invention, which is incorporated herein by reference.

BACKGROUND OF THE INVENTION

1. Field of the Invention

The present invention generally relates to the field of ultrasonic devices and, more particularly, to a method for improving the ability of an ultrasonic system to sweep and lock onto a resonance frequency of a blade subjected to a heavy load at startup.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat, as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostatis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop (that includes a voltage controlled oscillator, a frequency divider, a power switch, a matching network and a phase detector), stabilizes the frequency applied to the hand piece. A microprocessor controls the amount of power by sampling the frequency, current and voltage applied to the hand piece, because these parameters change with load on the blade.

The power versus load curve in a generator in a typical ultrasonic surgical system, such as that described in the Thomas patent, has two segments. The first segment has a positive slope of increasing power as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, continues to monitor the transducer current to voltage phase angle, and maintains the transducer resonating by driving it at the resonance frequency. A key function of such systems is to maintain the transducer resonating across load and temperature changes that vary the resonance frequency. However, these traditional ultrasonic drive systems have little or no flexibility with regards to adaptive frequency control. Such flexibility is key to the system's ability to discriminate undesired resonances. In particular, these systems can only search for resonance in one direction, i.e., with increasing or decreasing frequencies and their search pattern is fixed. The system cannot: (i) hop over other resonance modes or make any heuristic decisions, such as what resonance(s) to skip or lock onto, and (ii) ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

The ultrasonic system described in U.S. application Ser. No. 09/693,621, filed on Oct. 20, 2000, which is incorporated herein by reference, possesses the ability to sweep the output drive frequency, monitor the frequency response of the ultrasonic transducer and blade, extract parameters from this response, and use these parameters for system diagnostics. This frequency sweep and response measurement mode is achieved via a digital code such that the output drive frequency can be stepped with high resolution, accuracy, and repeatability not existent in prior art ultrasonic systems.

There are problems associated with existing ultrasonic systems. For example, such systems experience difficulty starting while the blade is under certain load conditions. Blade loading occurs when the blade comes into contact with skin tissue or as a result of debris getting between the blade and blade sheath. A major complaint of users of such ultrasonic generators is their failure to start under a moderate to heavy load. In the presence of a light to moderate load, debris between the blade and the blade sheath can load the blade such that startup or the ability of the blade to start in free standing air is degraded.

An acoustic system with minimal dampening level is more readily put into motion than one that is heavily loaded, i.e., damped. The electronics used to drive the transducer, operate best when used with a hand piece/blade which is easily put into motion. Higher voltages/currents more readily place a heavily loaded acoustic system into motion or into a more significant motion than lower voltages/currents, thereby providing a greater ability to initiate and lock onto resonance. However, it is not possible to achieve startup using such a hand piece/blade when it is subjected to a heavy load at a low voltage. Furthermore, a hand piece/blade which is successfully resonating and then placed under a heavy load can continue to resonate.

Generally, when an initial attempt to sweep over a frequency range and locate the resonance of the blade is performed, the voltage applied to the transducer is relatively low. This can result in either of the following conditions: First, a limitation experienced with startup under load results from an insufficient current feedback signal level. In this case, the impedance of the blade and the load are such that the voltage level applied to the hand piece at resonance produces a current feedback signal which is too small for the detection circuitry in the generator to read.

Second, another limiting factor is "sticktion," i.e., the blade getting stuck in the load. Here, the energy applied to the hand piece is insufficient to initiate blade motion, and the hand piece/blade responds as if there is a very large mechanical load. This condition may result in a highly damped hand piece/blade where the phase angle between the current and voltage never crosses zero, resulting an inability to detect resonance using zero crossing. Once the blade is in motion, this "static inertia" or "static frictional" force is no longer as great as it is at startup. At this point, the load can be increased or the drive signal decreased without causing a loss of resonance lock. A further limiting effect is gunking of the blade, i.e., the embedding of blood and other debris between the blade and the sheath to thereby load down the blade. The gunk itself loads the blade and decreases the capacity of the blade tip to successfully start under load.

Moreover, initially the primary intended resonance frequency of the blade is not known, therefore a sweep across a fairly wide frequency range is often performed by the generator. This "wide sweep" approach has several problems. First, locating the resonance is time consuming. If the sweep begins at one end of the sweep range, but the primary resonance is at the other end, a considerable amount of time is consumed to find the primary resonance. Second, it is possible to mistake a secondary resonance (a resonance not desired) for the primary resonance. Since there are other blade resonances (referred to herein as secondary resonances), the frequency sweep may encounter a secondary resonance before encountering the primary resonance. By limiting the sweep range, inadvertent locks onto the secondary resonances can be reduced. However, limiting the sweep range complicates blade design since the permitted primary resonance range of a blade becomes limited, and thus adds constraints to blade designs.

Another problem present in conventional ultrasonic devices is that the stability of the frequency control lock for power is affected by "ringing" of the transducer as the frequency approaches the resonance area of the blade.

SUMMARY OF THE INVENTION

The invention is a method for improving the ability of an ultrasonic system to sweep and lock onto a resonance frequency of a blade subjected to a heavy load at startup. This is accomplished by applying a high drive voltage or a high drive current. Increasing the drive signal to the hand piece results in an improved and more pronounced resonance as viewed when using a spectrum analyzer. That is, under load, the increased drive signal causes the maximum phase to become higher (more inductive), and the minimum impedance magnitude and the maximum impedance magnitude to respectively become lower and higher. Thus, increasing the excitation drive signal to the hand piece/blade at startup significantly alleviates the limiting factors associated with ultrasonic generators, which results in an increase of the maximum load capability at startup.

In accordance with the invention, the blade is driven with a progressively stronger signal, which permits a faster and more accurate identification of the actual operational resonance of the blade, and avoids inadvertently considering other resonance as the desired resonance frequency. Undesired resonance modes, such as transverse modes of resonance (i.e., a vibration along an axis which is perpendicular to the longitudinal axis of vibration of the hand piece/blade), are not excited until the energy levels which vibrate the blade are at a substantial level. This effect is advantageously utilized to initially ultrasonically drive the blade at very low levels across its known frequency range of resonance. The intended operational resonance of the blade is recognized by performing resonance impedance measurements during the sweep, and this impedance at resonance is more robust and discernable than other undesired resonances which require more energy to resonate efficiently. If no resonance is located, the drive intensity is increased and another sweep is performed. This method is repeated at sequentially higher drive levels until the blade resonance is acquired.

In an embodiment of the invention, a moderate to intense drive signal is applied to the blade during the sweep to locate the resonance frequency (rather than starting the sweep with a low level drive signal). If multiple resonances are encountered, the sweep is repeated at progressively lower levels until only one primary resonance is observed. Further, a method of using this embodiment of the present invention improves startup performance of the ultrasonic system while minimizing transducer ringing, which is especially noticeable under a "no-load" situation, when the system Q (i.e., the minimum system impedance) is high and the phase response slope in the phase-frequency plot is large. An additional benefit of starting the sweep at a high drive level is the ability to obtain a more robust resonance frequency of a heavily dampened blade which permits faster resonance frequency.identification and lock.

In another embodiment of the invention, a progressively wider sweep is performed, and a drive signal whose intensity is changed based on observed resonances. Such a combination provides the benefits of both a narrow sweep, which saves time, and high power, which assures it is possible to resonate a blade. For example, a narrow sweep at a high drive level is initially performed. If a resonance is not found, then the sweep is widened. If multiple resonances are found, the signal level is then reduced. Sweeping in this manner facilitates rapid identification of the desired resonance frequency of a dampened blade without inadvertently driving the blade at an undesired resonance frequency.

In an additional embodiment of the invention, the sweep for resonance is started from the most center or ideal resonance frequency for a blade. If no resonance is located, a check of frequencies at an increasing distance from the center or ideal frequency of the blade is performed, such as a very tight sweep which concentrates on a frequency range in the immediate vicinity of the ideal resonance frequency. If no resonance is found, then a check of the frequencies located slightly outward from the initial frequency range is performed. If no resonance is found here, then the swept frequency range is expanded and the search for the resonance frequency is again performed. To save time, each progressively wider frequency sweep skips frequencies previously covered, concentrating only on the unchecked frequencies within the revised wider range. Thus, identification of the resonance frequency is accelerated since most blades possess a primary resonance frequency which is closer statistically to the center or ideal frequency.

The method of the invention provides an ultrasonic system with the ability to start under a larger load. The method also provides the system with the ability to start faster and to lock onto the resonance frequency of the blade more readily, reduces problems related to "gunk" or debris lodged between the blade and sheath, and improves the loading capacity of the blade tip once it is applied to tissue. That is, the system will remain locked onto the resonance frequency of the blade during use under larger loads. In addition, a user will experience less difficulties during the operation of the ultrasonic surgical blade system because tissue loading capabilities and immunity to loss of lock due to "gunk" are significantly improved. Simplification of blade design is also achieved because secondary resonances can be placed at locations which are closer to the center or ideal resonance frequency of the blade without the traditional danger of the generator locking onto the secondary resonances. The design of the blade is further simplified because the primary resonance frequency of the blade can be placed further from the center frequency, yet still be identified through progressively wider searches for the resonance frequency.

BRIEF DESCRIPTION OF THE DRAWINGS

The foregoing and other advantages and features of the invention will become more apparent from the detailed description of the preferred embodiments of the invention given below with reference to the accompanying drawings in which.

DETAILED DESCRIPTION OF THE PREFERRED EMBODIMENTS

Figure 1:
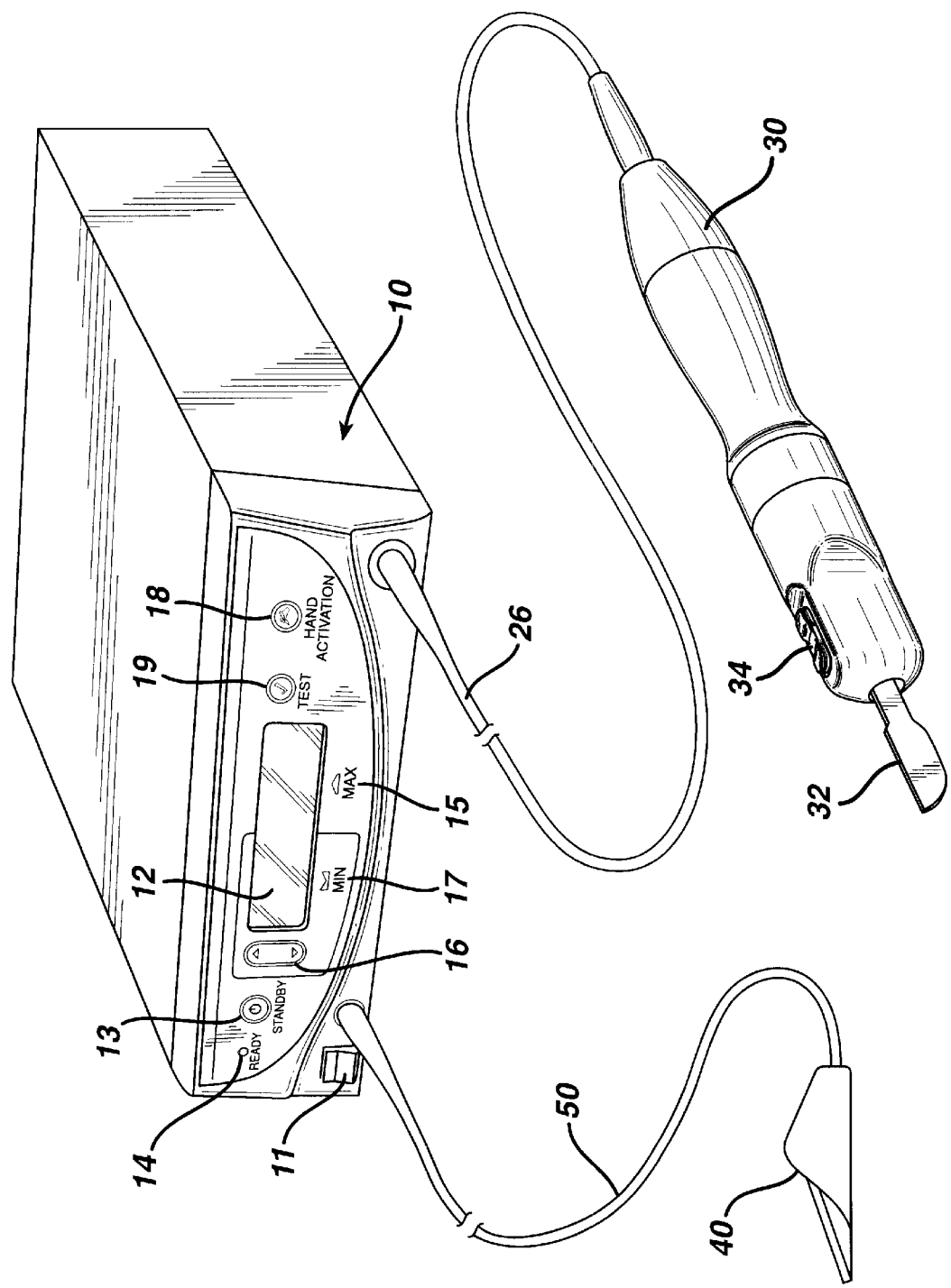
FIG. 1 is an illustration of a console for an ultrasonic surgical cutting and hemostatis system, as well as a hand piece and foot switch in which the method of the present invention is implemented.

FIG. 1 is an illustration of a system for implementing the method in accordance with the invention. By means of a first set of wires in cable 26, electrical energy, i e., drive current, is sent from the console 10 to a hand piece 30 where it imparts ultrasonic longitudinal movement to a surgical device, such as a sharp scalpel blade 32. This blade can be used for simultaneous dissection and cauterization of tissue. The supply of ultrasonic current to the hand piece 30 may be under the control of a switch 34 located on the hand piece, which is connected to the generator in console 10 via wires in cable 26. The generator may also be controlled by a foot switch 40, which is connected to the console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means such, as percentage of maximum cutting power or numerical power levels associated with cutting power. The liquid crystal display device 12 can also be utilized to display other parameters of the system. Power switch 11 is used to turn on the unit. While it is warming up, the "standby" light 13 is illuminated. When it is ready for operation, the "ready" indicator 14 is illuminated and the standby light goes out. If the unit is to supply maximum power, the MAX button 15 is depressed. If a lesser power is desired, the MIN button 17 is activated. The level of power when MIN is active is set by button 16.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

Figure 2:
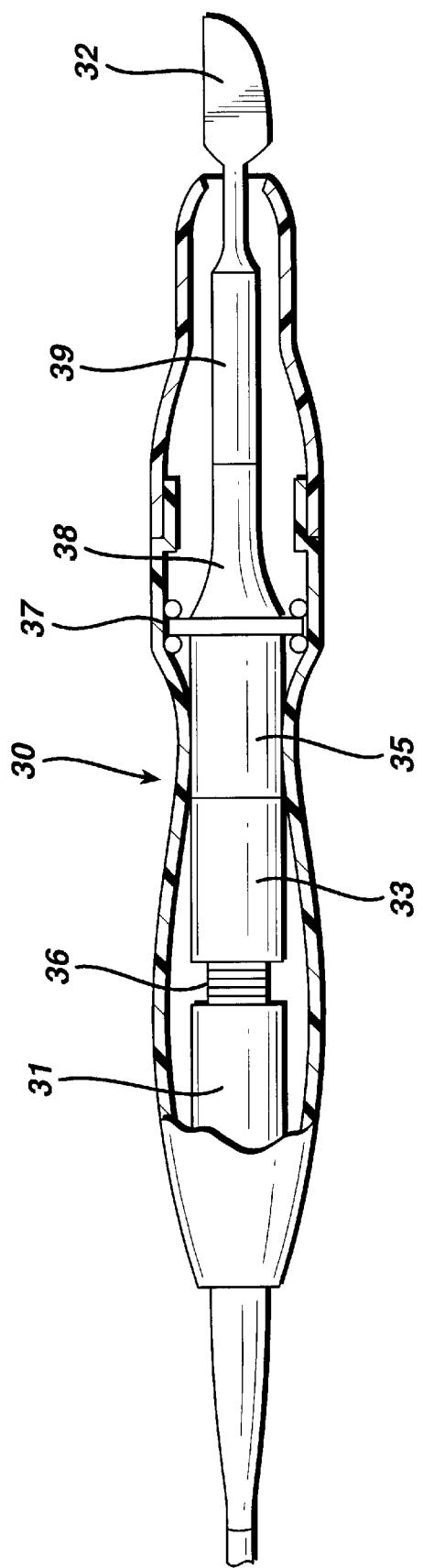
FIG. 2 is a schematic view of a cross section through the ultrasonic scalpel hand piece of the ultrasonic surgical cutting and hemostatis system of FIG. 1.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which in turn is mounted to the housing at another motion null point 37. A horn 38 is also attached to the null point on one side and to a coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion with a portion of the stack constituting a motionless node, when the transducer is driven with a maximum current at the transducers' resonant frequency. However, the current providing the maximum motion will vary with each hand piece and is a valve stored in the non-volatile memory of the hand piece so the system can use it.

The parts of the hand piece are designed such that the combination will oscillate at the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus, the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32. A motion at the transducer stack is amplified by the horn 38 into a movement of about 20 to 25 microns. A motion at the coupler 39 is amplified by the blade 32 into a blade movement of about 40 to 100 microns.

Figure 3A:
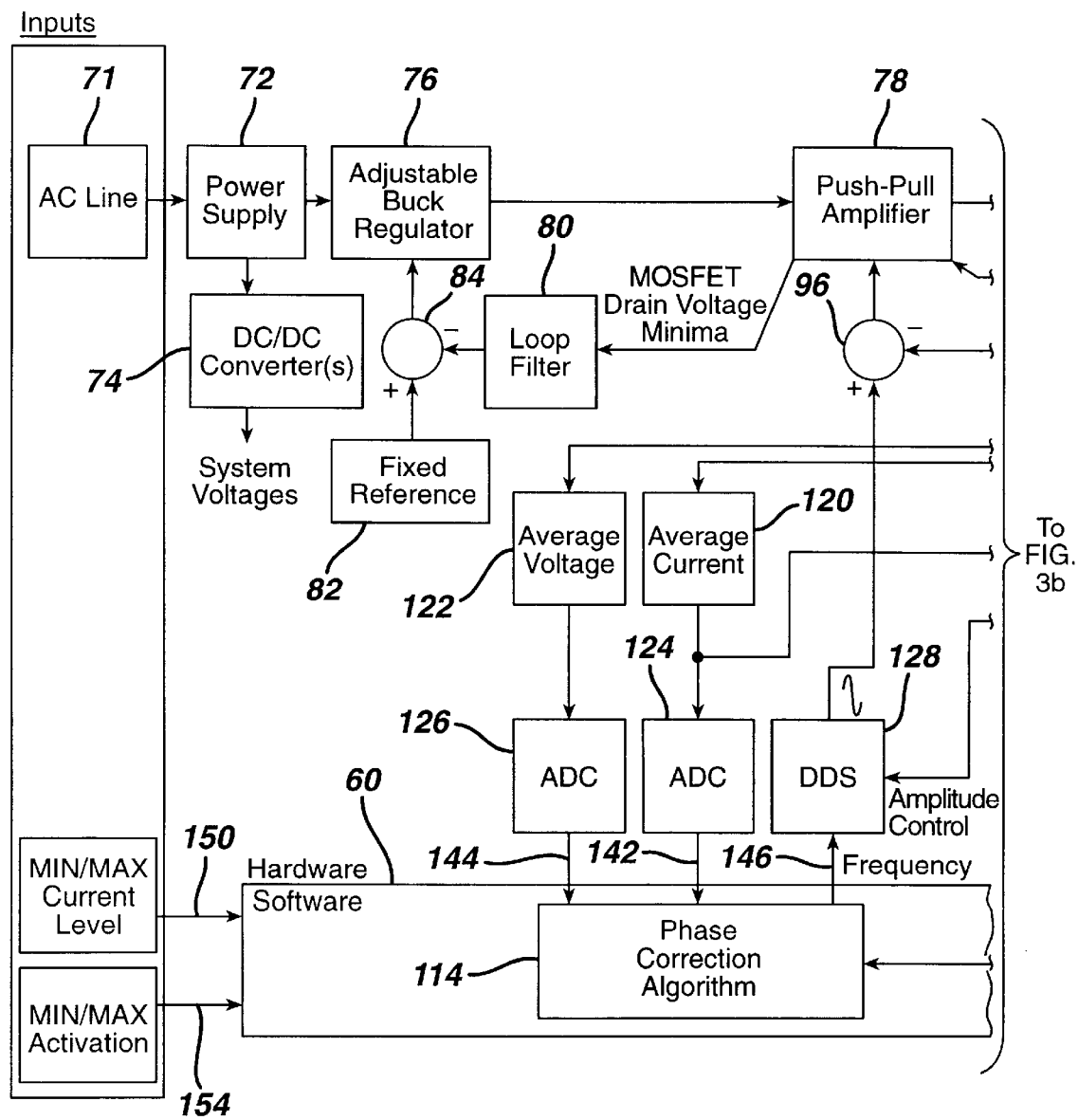
FIGS. 3(a) and 3(b) is a block diagram illustrating a system for driving the transducer in the hand piece of ultrasonic surgical cutting and hemostatis system of FIG. 1.
Figure 3B:
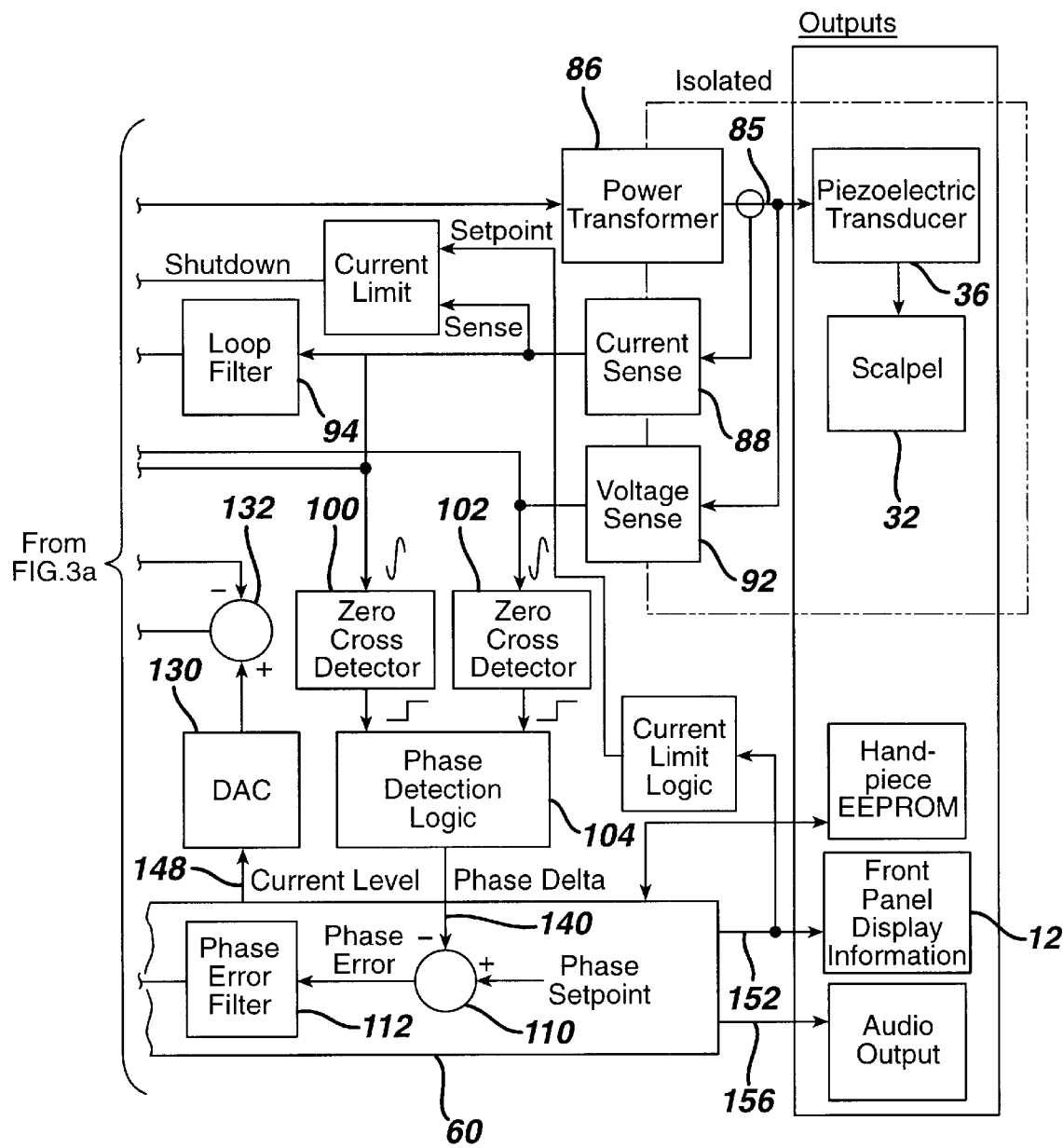

The system which creates the ultrasonic electrical signal for driving the transducer in the hand piece is illustrated in FIGS. 3(*a*) and 3(*b*). This drive system is flexible and can create a drive signal at a desired frequency and power level setting. A DSP 60 or microprocessor in the system is used for monitoring the appropriate power parameters and vibratory frequency as well as causing the appropriate power level to be provided in either the cutting or coagulation operating modes. The DSP 60 or microprocessor also stores computer programs which are used to perform diagnostic tests on components of the system, such as the transducer/blade.

For example, under the control of a program stored in the DSP or microprocessor 60 such as a phase correction algorithm, the frequency during startup can be set to a particular value, e.g., 50 kHz. It can then be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is a undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located. In any event, the system has a great degree of flexibility.

In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3(*b*)) to the console front panel display 12. Further, the DSP or microprocessor 60 generates a digital current level signal 148 that is converted to an analog signal by digital-to-analog converter (DAC) 130. The resulting reference analog signal is applied as a current set point to summing node 132. A signal representing the average output current from circuit 120 is applied to the negative input of node 132. The output of node 132 is a current error signal or amplitude control signal which is applied to direct digital synthesis (DDS) circuit 128 to adjust the amplitude of its output, as opposed to the frequency of its output, which is controlled by the signal on line 146 from the DSP or microprocessor 60. The arrangement of current level signal 148, DAC 130, summing node 130, and signal supplied by average output voltage 122 allows the DSP or microprocessor 60 to adjust the output current such that it can generate a desired power versus load curve when not in constant current mode.

To actually cause the surgical blade to vibrate, the user activates the foot switch 40 or the hand piece switch 34. This activation puts a signal on line 154 in FIG. 3(*a*). This signal is effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

Under control of the program stored in the DSP or microprocessor 60 in the system shown in FIGS. 3(*a*) and 3(*b*), the method of the invention is implemented by sweeping the transducer 36 at a higher voltage level such as 140 volts or at a higher current level to over come a load on the blade, e.g., "drag" and inertial effects upon the blade 32 which are present during startup, and to induce a motion which is sufficient to evoke a resonating action which can be recognized and locked onto. A heavily loaded blade results in a highly dampened system, in which the transducer impedance is relatively high. A higher voltage permits more current to flow through the relatively high impedance so that adequate current flow occurs which can be readily measured. The DSP 60 or microprocessor is used to monitor the appropriate parameters, which in this case is the transducer resonance frequency, which is indicated by the frequency maximum phase or the minimum impedance magnitude.

Figure 4:
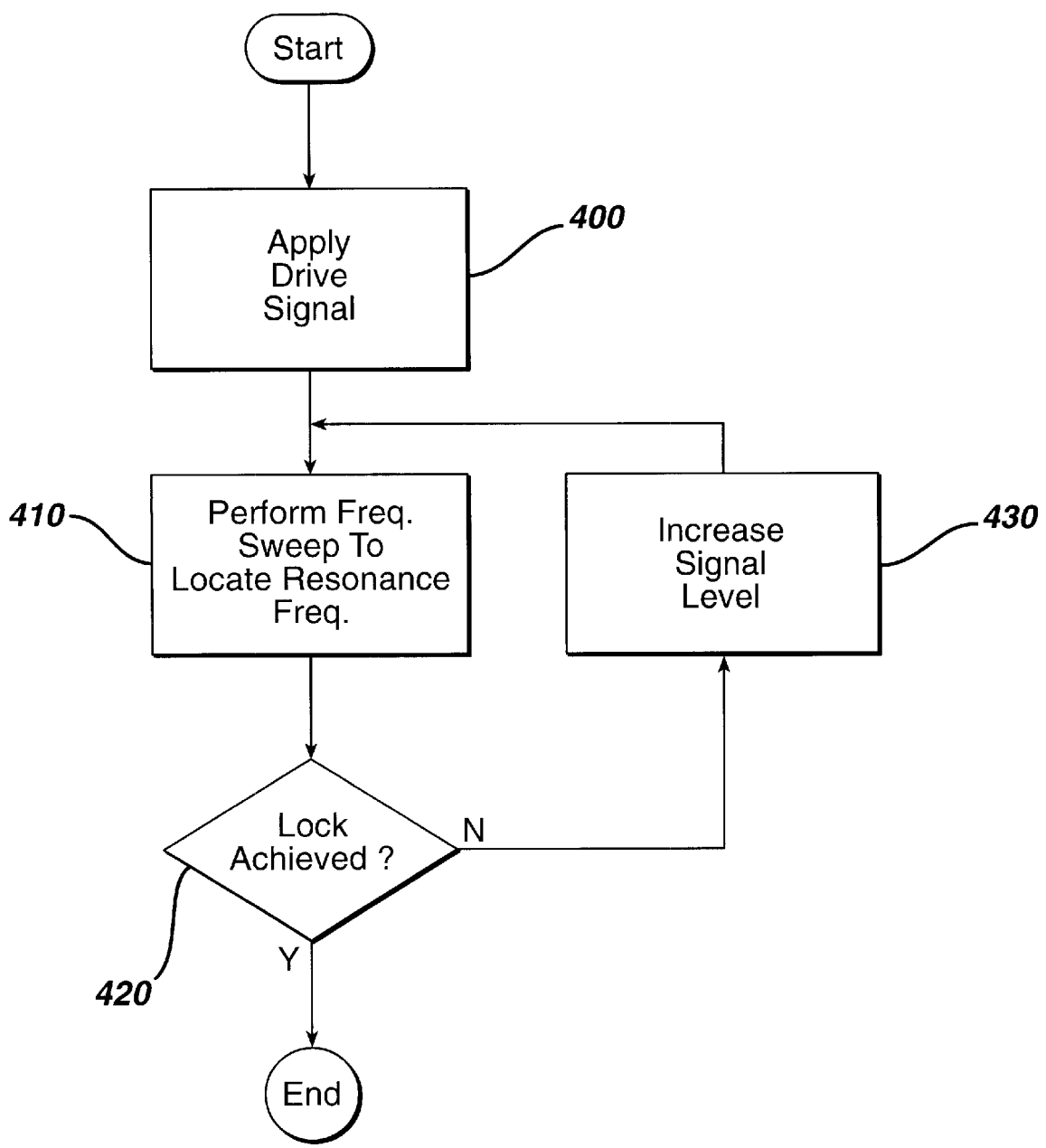
FIG. 4 is a flow chart of a preferred embodiment of the method of the invention.

FIG. 4 is flow chart illustrating a preferred embodiment of the method of the invention. In step 400, a drive signal is initially applied to the hand piece/blade. In step 410, a frequency sweep is performed to locate the resonance frequency of the hand piece/blade. A check is performed to determine whether the DSP or microprocessor 60 has achieved lock, as indicated in step 420. If lock is achieved, the method is terminated. If the DSP or microprocessor 60 fails to achieve lock, in step 430 the level of the drive signal is increased, and step 410 is repeated. In this manner, the method will continue in the "loop" until the DSP or microprocessor 60 achieves lock.

In an alternative embodiment of the invention, startup under load is performed with progressively higher currents/voltages during each sweep until a lock onto the resonance frequency of the blade 36 occurs. As a result, driving the blade 36 with too large a signal is avoided, which can result in inadvertent blade displacement overshoots due to limitations of the feedback control circuit. The intended operational resonance of the blade is recognized by performing resonance impedance measurements during the sweep. Thus, after failing to locate the blade resonance after sweeping over the frequency range of interest using a specific drive current, the attempt to find resonance is performed with a higher current level. These steps are repeated at sequentially higher drive levels until the blade resonance is acquired. Alternatively, the maximum phase or the minimum magnitude of impedance over a specific frequency range can be found, and the drive current at this frequency increased such that resonance is detected. Upon location of the resonance frequency, the current drive signal is reduced as needed to the required operating level. In this manner, a faster and more accurate identification of the actual operational resonance of the blade, and an avoidance of inadvertent considerations of other resonances is achieved.

Figure 5:
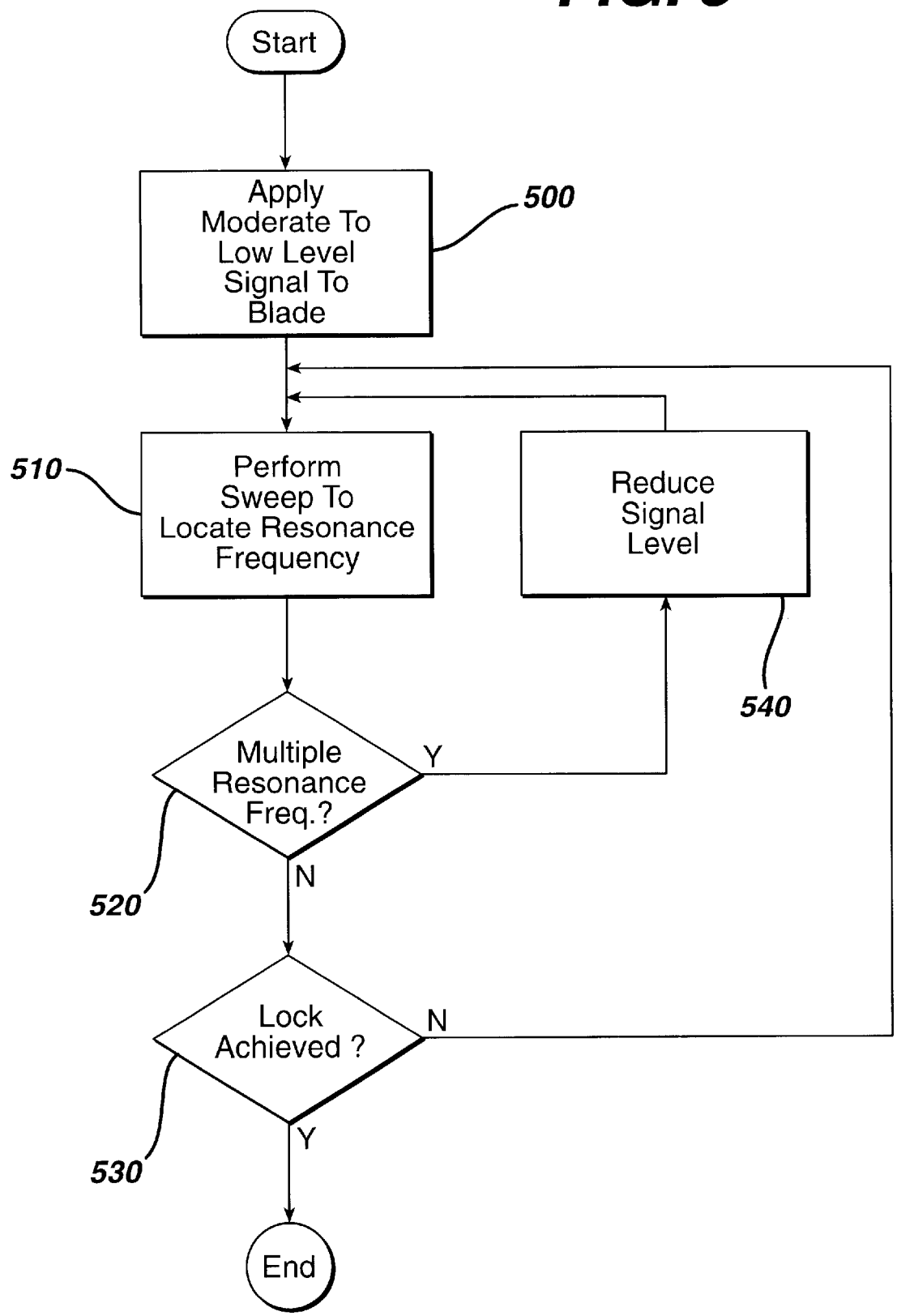
FIG. 5 is a flow chart of an alternative embodiment of the method of FIG. 4.

FIG. 5 is a flow chart illustrating an alternative embodiment of the method of the invention. In this case, rather than starting the sweep at a low drive level, a moderate to intense drive signal is applied to the blade. As shown in step 500, the drive signal is initially applied to the hand piece/blade. In step 510, a frequency sweep is performed to locate the resonance frequency of the hand piece/blade. In step 520, a check is performed to determine whether multiple resonances are present in the hand piece/blade. In step 540, if multiple resonances are present, the level of the drive signal is reduced, and a return to step 510 occurs. If multiple resonances are not present in the hand piece/blade, a check is performed to determine whether the DSP or microprocessor 60 has achieved lock, as indicated in step 530. If lock is achieved, the method is terminated. If the DSP or microprocessor 60 fails to achieve lock, in step 540 the level of the drive signal is increased, and step 510 is repeated. In this manner, the method will continue "looping"until only one primary resonance is observed to thereby permit the DSP or microprocessor 60 to achieve lock. Sweeping in this manner results in a substantial reduction of processing time. An additional benefit of starting the sweep at a high drive level is the ability to obtain a more robust resonance frequency of a heavily dampened blade which permits faster resonance identification and lock.

Figure 6:
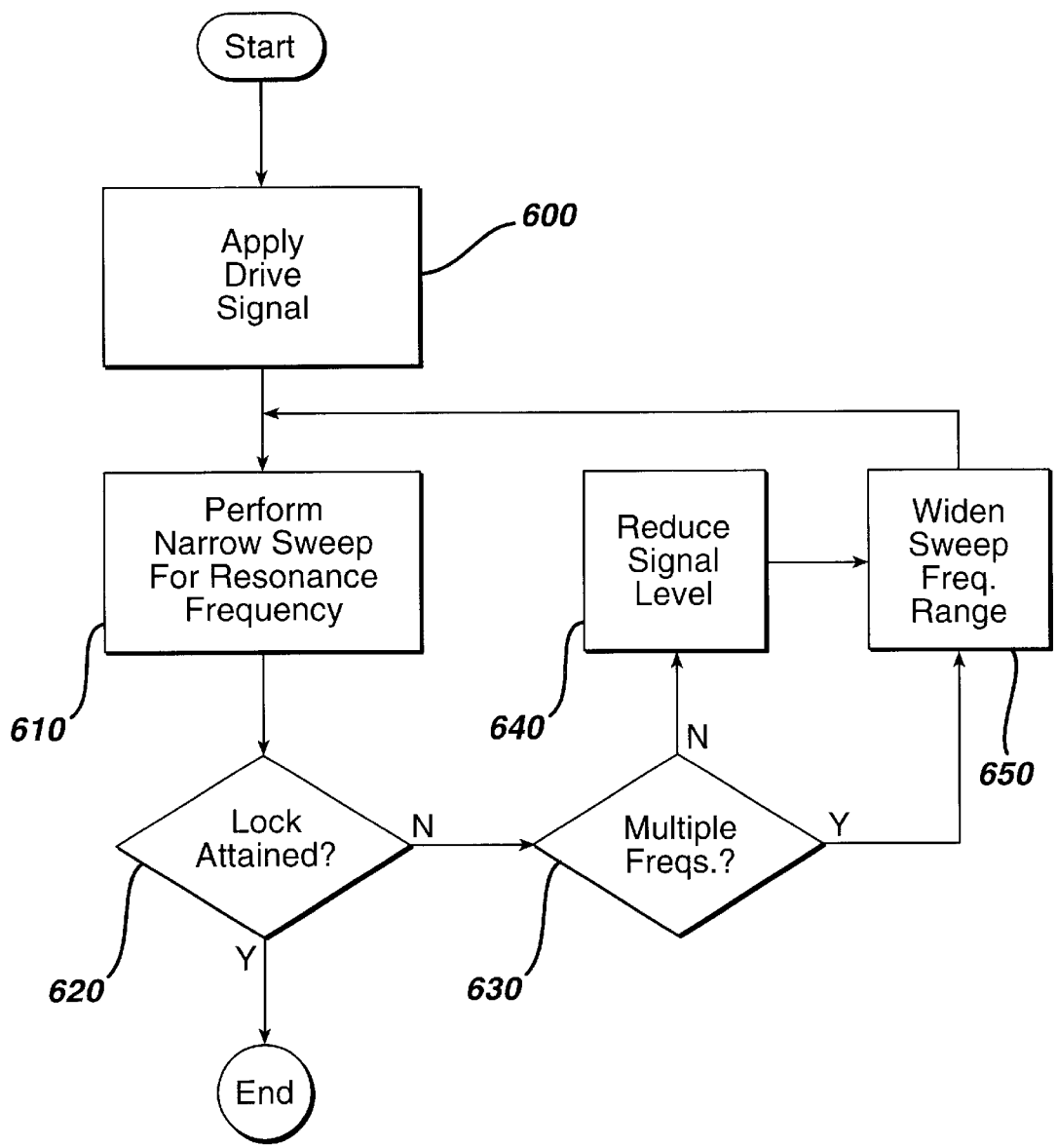
FIG. 6 is a flow chart of another embodiment of the method of FIG. 4.

FIG. 6 is a flow chart illustrating another embodiment of the method of the invention. Here, a progressively wider sweep is performed and a drive signal having a progressively upwardly ramped intensity is used to drive the blade. Such a combination provides the benefits of both a narrow sweep which save time and high power which assures it is possible to resonate a blade. In step 600, a drive signal is applied to the hand piece/blade. As shown in step 610, a narrow frequency sweep is performed to locate the resonance frequency of the hand piece/blade. A check is performed to determine whether the DSP or microprocessor 60 has achieved lock, as indicated in step 620. If lock is achieved, then the method is terminated. If lock is not achieved, a check is performed to determine whether multiple resonances are present in the hand piece/blade, as indicated in step 630. If multiple resonances are not present in the hand piece/blade, in step 640 the input signal is increased and the method proceeds to step 650. If multiple resonances are present in the hand piece/blade, the method will proceed directly to step 650, where the frequency sweep range is decreased prior to returning to step 610. The method will continue "looping" in this manner until the DSP or microprocessor 60 achieves lock. The present embodiment facilitates rapid identification of the desired resonance of a dampened blade without inadvertently driving the blade at undesired resonances.

Figure 7:
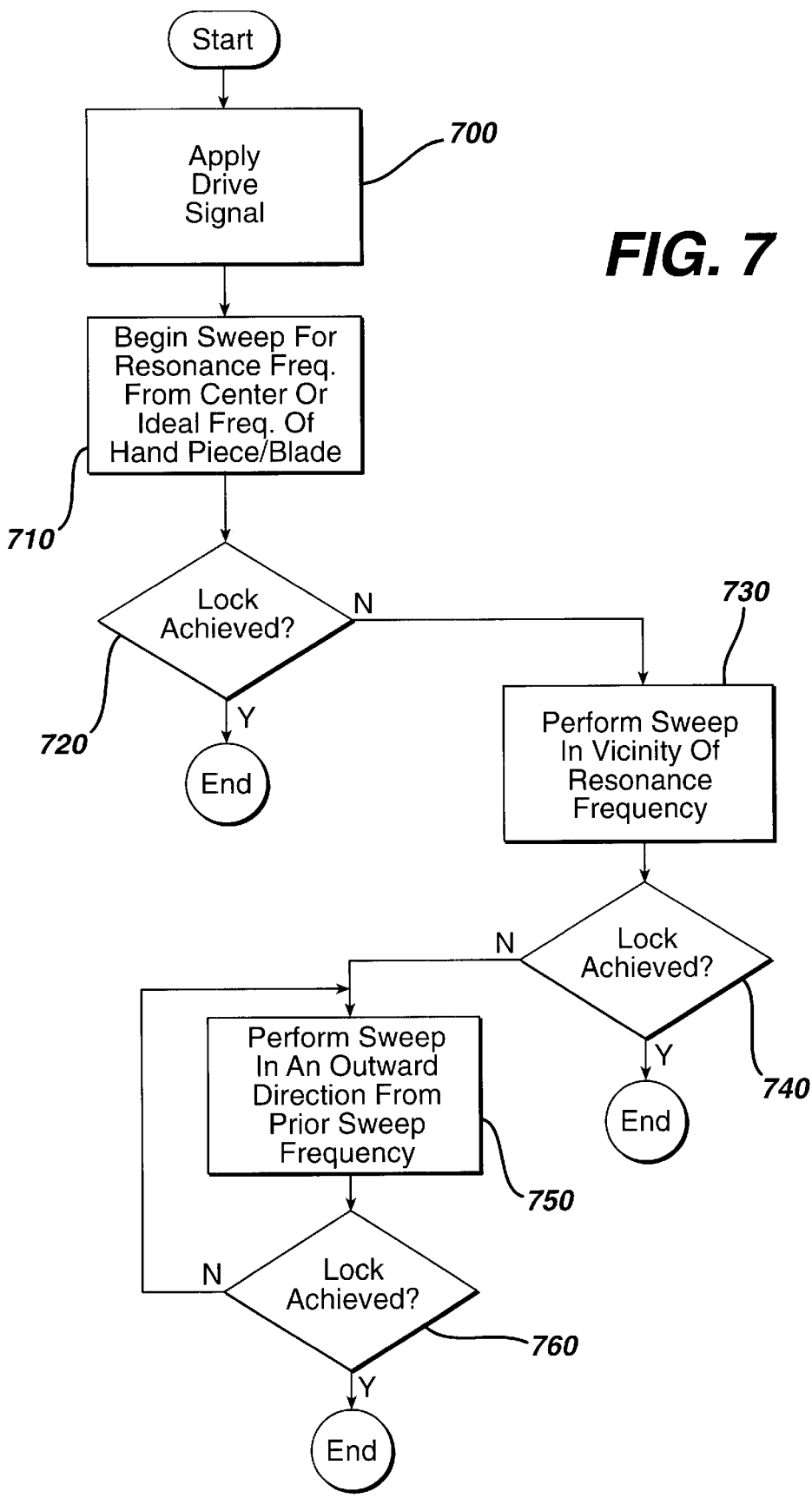
FIG. 7 is a flow chart of an embodiment of the method of FIG. 4.

FIG. 7 is a flow chart illustrating a further embodiment of the method of the invention. In the present embodiment, the sweep for resonance is started from the most center or ideal resonance frequency for a blade. As shown in step 700, a drive signal is initially applied to the hand piece/blade. In step 710, beginning from the ideal or center resonance frequency for the hand piece/blade, a frequency sweep is performed to locate the resonance frequency of the hand piece/blade. In step 720, a check is performed to determine whether the DSP or microprocessor 60 has achieved lock. If lock is achieved, then the method is terminated. If lock is not achieved, in step 730 a sweep is performed in the approximate vicinity of the resonance frequency of the hand piece/blade. A check is again performed to determine whether the DSP or microprocessor 60 has achieved lock, as indicated in step 740. If lock is achieved, the method is terminated.

In step 750, if lock is not achieved, a sweep is performed in an outward direction (i.e., the frequency range is increased) from the prior sweep frequency. In step 760, a check is again performed to determine whether the DSP or microprocessor 60 has achieved lock. If lock is achieved, then the method is terminated. If lock is not achieved, a return to step 750 occurs. The method will continue "looping" in this manner until the DSP or microprocessor 60 achieves lock. To save time, each progressively wider frequency sweep skips frequencies previously covered, concentrating only on the unchecked frequencies within the revised wider range. Thus, identification of the resonance frequency is accelerated since most blades possess a primary resonance frequency which is closer to the center or ideal frequency of the hand piece/blade.

Using the method of the invention, accelerated resonance frequency sweeps are achieved. This is partly due to the more robust electrical response of the transducer/acoustic system when driven by a greater voltage/current, which results in a transducer response which is more pronounced. Moreover, signal tracking is more easily achieved and resonance.frequency lock is more readily obtained.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for driving an ultrasonic system to improve acquisition of blade resonance at start up, comprising the steps of:

applying a drive signal to an ultrasonic hand piece/blade using an ultrasonic generator;

performing a frequency sweep to locate a resonance frequency of the blade;

determining whether a microprocessor located in the generator has acquired the resonance frequency of the blade; and if the microprocessor failed to acquire the resonance frequency of the blade, increasing the drive signal level and continuing to perform frequency sweeps until the microprocessor acquires the resonance frequency of the blade.

2. The method of claim 1, wherein the step of applying the drive signal comprises exciting the hand piece/blade with an ultrasonic signal at a predetermined drive frequency.

3. The method of claim 2, wherein the drive signal has a voltage level of approximately 140 volts.

4. The method of claim 1, wherein start up under load is performed at progressively higher drive currents/voltages levels during each sweep until a lock onto the resonance frequency of the blade occurs.

5. A method for driving an ultrasonic system to improve acquisition of hand piece/blade resonance at start up, comprising the steps of:

applying a moderate to intense drive signal to an ultrasonic hand piece/blade using an ultrasonic generator;

performing a frequency sweep to locate a resonance frequency of the hand piece/blade;

determining whether multiple resonance frequencies are present in the hand piece/blade;

if multiple resonances are present in the hand piece/blade, reducing the drive signal level and continuing to perform frequency sweeps;

if multiple resonances are not present in the hand piece/blade, checking to determine whether a microprocessor located in the generator has failed to acquire the resonance frequency of the hand piece/blade; and if the microprocessor failed to acquire the resonance frequency of the hand piece/blade, increasing the drive signal level and continuing to perform frequency sweeps until the microprocessor acquires the resonance frequency of the blade.

6. A method for driving an ultrasonic system to improve acquisition of hand piece/blade resonance at start up, comprising the steps of:

applying a drive signal to an ultrasonic hand piece/blade using an ultrasonic generator;

performing a narrow frequency sweep to locate a resonance frequency of the hand piece/blade;

determining whether a microprocessor located in the generator has acquired the resonance frequency of the blade;

if the microprocessor failed to acquire the resonance frequency of the hand piece/blade, determining whether multiple resonance frequencies are present in the hand piece/blade;

if multiple resonances are not present in the hand piece/blade, increasing the drive signal level and increasing the sweep frequency;

if multiple resonances are present in the hand piece/blade, decreasing the frequency sweep range; and returning to the step of performing the narrow frequency sweep to locate a resonance frequency of the hand piece/blade.

7. A method for driving an ultrasonic system to improve acquisition of hand piece/blade resonance at start up, comprising the steps of:

applying a drive signal to an ultrasonic hand piece/blade using an ultrasonic generator;

performing a frequency sweep from an ideal frequency for the hand piece/blade to locate a resonance frequency of the hand piece/blade;

determining whether a microprocessor located in the generator has acquired the resonance frequency of the blade;

if the microprocessor failed to acquire the resonance frequency of the hand piece/blade, performing a sweep in an approximate vicinity of the ideal frequency for the hand piece/blade;

determining whether the microprocessor has acquired the resonance frequency of the blade;

if the microprocessor failed to acquire the resonance frequency of the hand piece/blade, performing the frequency sweep in an outward direction from a prior sweep frequency;

determining whether the microprocessor has acquired the resonance frequency of the blade; and returning to the step of performing the frequency sweep in an outward direction from the prior sweep frequency, if the microprocessor failed to acquire the resonance frequency of the hand piece/blade.

8. The method of claim 7, wherein the ideal frequency is approximately 55 kHz.

9. The method of claim 8, wherein said performing the frequency sweep in an outward direction from the prior sweep frequency comprises increasing a sweep frequency range.

* * * * *